«12» United States Patent
Draper et al.

«10» Patent No.: US 12,186,538 B1
«45» Date of Patent: Jan. 7, 2025

«54» ELECTRONIC ADD-ON MODULE AND ASSEMBLY OF AN ELECTRONIC ADD-ON MODULE AND A DRUG DELIVERY DEVICE

«71» Applicant: Sanofi, Paris (FR)

«72» Inventors: Paul Richard Draper, Warwickshire (GB); Andrew Wallace, Warwickshire (GB); Aidan Michael O'Hare, Warwickshire (GB); Robert Frederick Veasey, Warwickshire (GB)

«73» Assignee: Sanofi, Paris (FR)

« * » Notice: Subject to any disclaimer, the term of this patent is extended or adjusted under 35 U.S.C. 154(b) by 0 days.

«21» Appl. No.: 18/660,854

«22» Filed: May 10, 2024

«51» Int. Cl.
*A61M 5/315* (2006.01)
*A61M 5/31* (2006.01)

«52» U.S. Cl.
CPC . *A61M 5/31546* (2013.01); *A61M 2005/3126* (2013.01); *A61M 2205/3306* (2013.01)

«58» Field of Classification Search
CPC .. A61M 2005/3126; A61M 2005/3125; A61M 5/31546; A61M 5/31525; A61M 5/31553; A61M 5/31568; A61M 5/31551; A61M 2205/3306
See application file for complete search history.

«56» References Cited

U.S. PATENT DOCUMENTS

| | | | |
|---|---|---|---|
| 5,693,027 A | 12/1997 | Hansen et al. | |
| 6,663,602 B2 | 12/2003 | Moller | |
| 7,241,278 B2 | 7/2007 | Moller | |
| 9,937,294 B2 | 4/2018 | Quinn et al. | |
| 11,554,221 B2 | 1/2023 | Byerly et al. | |
| 2020/0405968 A1* | 12/2020 | Pedersen | A61M 5/31551 |
| 2023/0347066 A1 | 11/2023 | Marcoz | |

FOREIGN PATENT DOCUMENTS

| | | |
|---|---|---|
| EP | 1570876 B1 | 12/2009 |
| EP | 2814547 B1 | 7/2015 |
| EP | 3164173 A1 | 5/2017 |
| EP | 2890434 B1 | 4/2020 |
| WO | WO 2004/068820 A2 | 8/2004 |
| WO | WO 2004/078239 A1 | 9/2004 |
| WO | WO 2005/018629 A1 | 3/2005 |
| WO | WO 2005/018721 A1 | 3/2005 |

(Continued)

OTHER PUBLICATIONS

Hamers-Casterman et al., "Naturally occurring antibodies devoid of light chains," Nature, Jun. 3, 1993, 363(6428):446-448.

(Continued)

*Primary Examiner* — Tasnim Mehjabin Ahmed
«74» *Attorney, Agent, or Firm* — Fish & Richardson P.C.

«57» ABSTRACT

An electronic add-on module configured for releasable attachment to a drug delivery device is described. The electronic add-on module includes at least a body configured to be releasably attached to the device housing, a coupler configured to be releasably attached to the device dial grip, and a dial configured to be axially displaceable with respect to the coupler. The electronic add-on module further includes a tube which is configured to be permanently rotationally constrained to the body and configured to be axially displaceable relative to the body wherein the dial is configured to be rotatable relative to the tube at least in a dialing mode.

20 Claims, 7 Drawing Sheets

(56) References Cited

FOREIGN PATENT DOCUMENTS

| WO | WO 2006/003388 A2 | 1/2006 |
|---|---|---|
| WO | WO 2006/030220 A1 | 3/2006 |
| WO | WO 2009/132777 A1 | 11/2009 |
| WO | WO 2014/033195 A1 | 3/2014 |
| WO | WO 2016/198516 A1 | 12/2016 |
| WO | WO 2019/101962 A1 | 5/2019 |
| WO | WO 2019/162235 A1 | 8/2019 |
| WO | WO 2021/260404 A1 | 12/2021 |
| WO | WO 2023/046787 A1 | 3/2023 |
| WO | WO 2023/099514 A1 | 6/2023 |
| WO | WO 2023/169924 A1 | 9/2023 |

OTHER PUBLICATIONS

Holt et al., "Domain antibodies: proteins for therapy," Trends in Biotechnology, Nov. 2003, 21(11):484-490.

Muyldermans, "Single domain camel antibodies: current status," Reviews in Molecular Biotechnology, Jun. 2001, 74(4):277-302.

Needle-based injection systems for medical use Requirements and test methods, Part 1: Needle injection systems, ISO 11608-1:2014(E), Third Edition, Switzerland, ISO, Dec. 15, 2014, pp. 1-13.

Ward et al., "Binding activities of a repertoire of single immunoglobulin variable domains secreted from *Escherichia coli*," Nature, Oct. 1, 1989, 341(6242):544-546.

\* cited by examiner

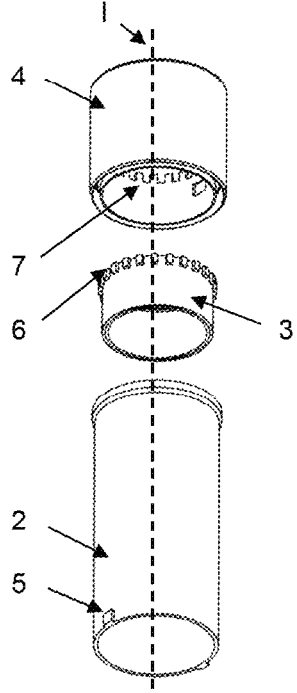
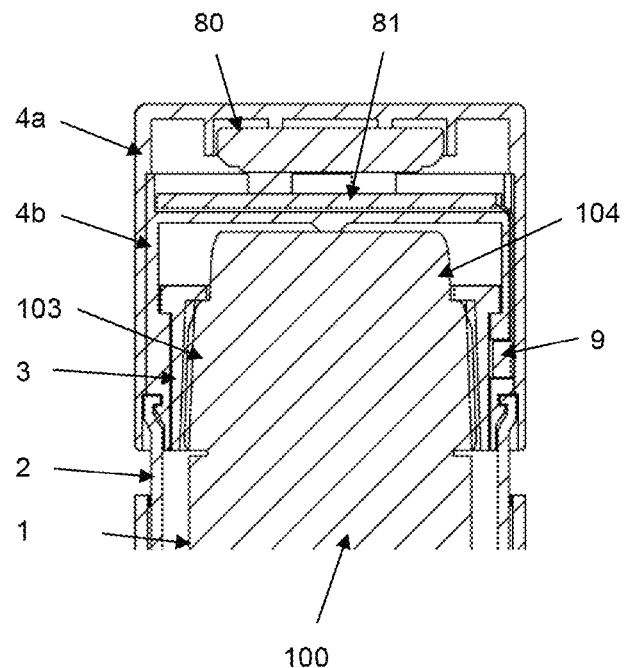
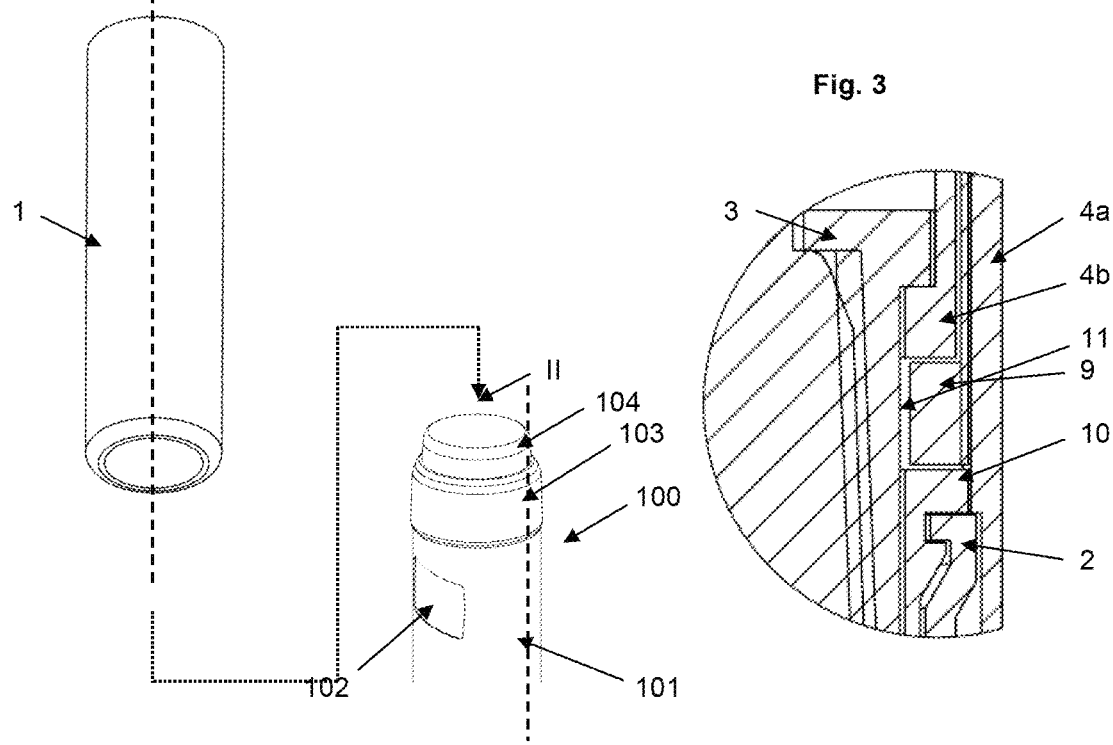

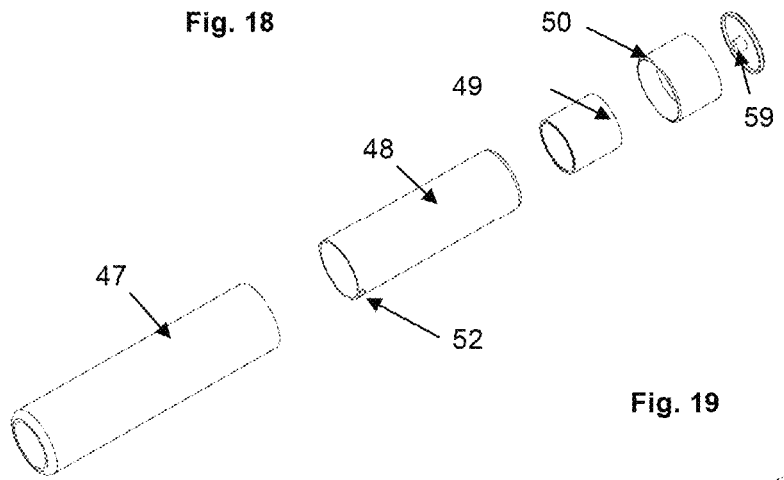
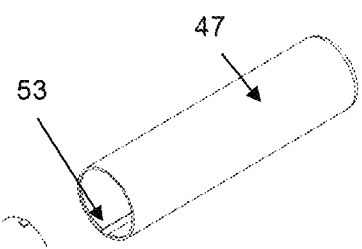
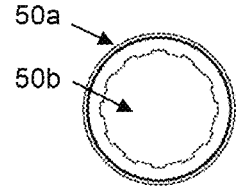
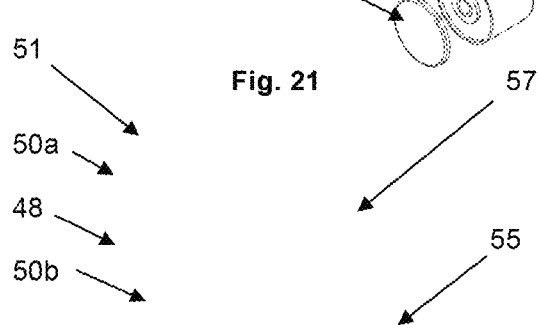
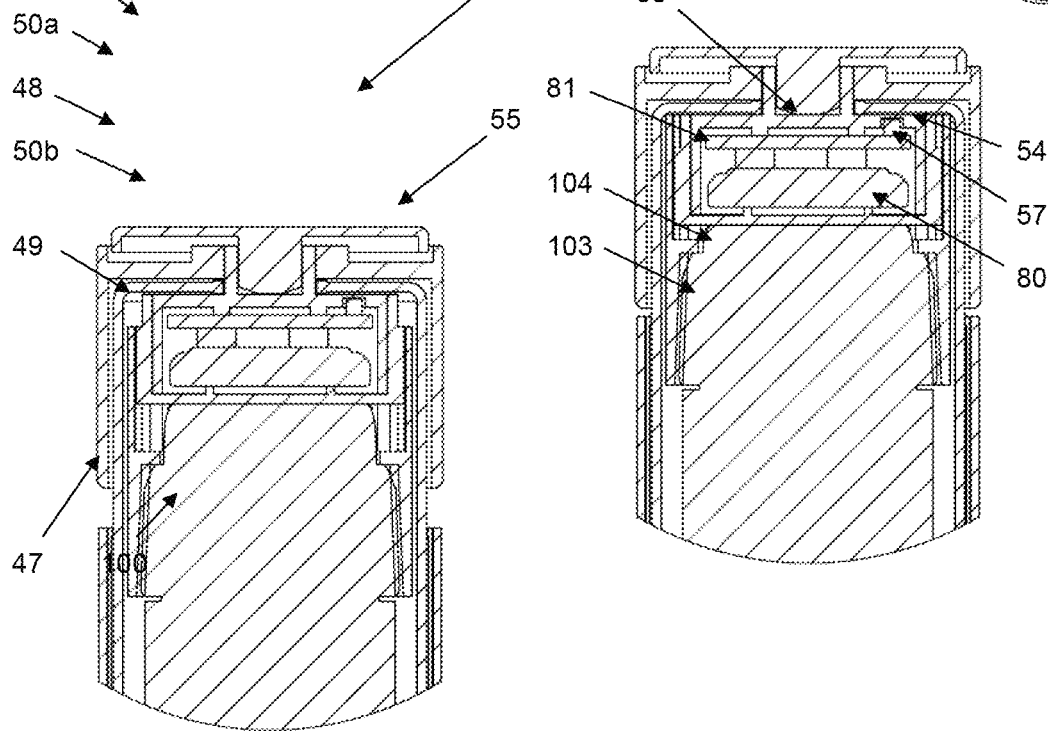

ELECTRONIC ADD-ON MODULE AND ASSEMBLY OF AN ELECTRONIC ADD-ON MODULE AND A DRUG DELIVERY DEVICE

TECHNICAL FIELD

The present disclosure is generally directed to an electronic add-on module and to an assembly of an electronic system, e.g. an electronic add-on module, which is configured to be releasably attached to a drug delivery device.

BACKGROUND

A variety of diseases exists that require regular treatment by injection of a medicament. Such injection can be performed by using injection devices (drug delivery devices), which are applied either by medical personnel or by patients themselves. As an example, type-1 and type-2 diabetes can be treated by patients themselves by injection of insulin doses, for example once or several times per day. For instance, a pre-filled disposable insulin pen can be used as an injection device. Alternatively, a re-usable pen may be used. A reusable pen allows replacement of an empty medicament cartridge by a new one. Some drug delivery devices only allow injection of a previously fixed dose (so-called fixed dose devices). In other devices (so-called variable dose devices) the medicament dose to be injected can be manually selected at the injection device by turning a dosage knob, often referred to as dial grip, and observing the actual dose from a dose window or display of the injection device. The dose is then injected by inserting the needle into a suited skin portion and pressing an injection button of the injection device. Known drug delivery devices are explained in more detail for example in EP 1 570 876 B1, EP 2 814 547B1, EP 2 890 434 B1, EP 3 164 173 A1, WO 2005/018721 A1, WO 2009/132777 A1, WO 2014/033195 A1, U.S. Pat. Nos. 5,693,027 A, 6,663,602 B2, 7,241,278 B2 or U.S. Pat. No. 9,937,294 B2.

To be able to monitor medicament injection, for instance to prevent false handling of the insulin pen or to keep track of the doses already applied, it is desirable to measure information related to a condition and/or use of the injection device, such as for instance information on the injected medicament dose. For example electronic add-on modules are known which measure relevant data with respect to dose setting and/or dose dispensing. An exemplary data collection device for attachment to an injection device is for example shown in WO 2016/198516 A1. This data collection device is configured as a cap which can be attached onto a dial grip of a drug delivery device. The device of WO 2016/198516 A1 is applicable to drug delivery devices providing a sufficient rotational reference to the stationary components of the drug delivery device. However, some known drug delivery devices do not have relatively rotating components easily accessible to the module. Without this rotational reference the dose recording of the electronic module might be susceptible to errors caused by rotations induced by the user when dispensing.

Another add-on module is known from WO 2021/260404 A1. This module comprises a portion which is fixed to the stationary outer housing of the drug delivery device and another portion which is fixed to the rotatable dial grip of the drug delivery device. The module comprises a magnetic field production means and a plurality of magnetic sensors and is configured to calculate and determine whether or not all of the dose or amount set by the user of the drug delivery device has been ejected from the drug delivery device. This module can only be used with a drug delivery device having an axially stationary dial grip, i.e. without a so-called dial extension during dose dialing.

SUMMARY

Using the detection of relative movements often requires further, especially structural, modifications to the drug delivery device as movements of components inside the drug delivery device may best to be sensed in order to gather relevant dose event information. These structural modifications, for example the provision of encoder patterns, are less suitable for retrofitting a drug delivery device with an electronic add-on module.

Consequently, there is a need to provide an electronic add-on module which may be used with a variety of different drug delivery devices without requiring structural modifications of the drug delivery devices. In addition, the subject matter of this disclosure provides an improved electronic add-on module that is configured to detect dose events of different drug delivery devices in a reliable and safe manner.

An electronic add-on module according to the present disclosure is configured for releasable attachment to an, e.g. pen injector type, drug delivery device, especially to a device housing and a device dial grip. The electronic add-on module may comprise at least a body configured to be releasably attached to the device housing, a coupler configured to be releasably attached to the device dial grip, and a dial configured to be axially displaceable with respect to the body and, optionally with respect to the coupler. In other words, the present disclosure is based on the overarching principle to attach part of the module to the housing of the pen injector and part of the module to the dial grip of the pen injector. The electronic add-on module may be configured to be switched between a dialing mode and a dispensing mode by means of an axial displacement of the dial relative to the body. Typically, in the dialing mode, the dial is rotationally constrained to the coupler in order to transmit a torque applied by a user to the dial via the coupler to the device dial grip. Further, in the dispensing mode, an axial displacement of the dial relative to the body may be transmitted to a device dial grip or to a separate device button which then may cause or trigger dose dispensing from the drug delivery device.

There are two main issues that can be solved with such an arrangement. Firstly, if the electronic module only attaches to the device dial grip, as is typical with other modules, then no rotational reference to the stationary components of the pen injector is accessible. Without this rotational reference then the dose recording of the electronic module is susceptible to errors caused by rotations induced by the user when dispensing. Attaching part of the module to the device housing gives a means to reference the rotational measurement of the system relative to the stationary device housing. Secondly, if the electronic module attaches only to the device dial grip of specific pen injectors, then there may be no relatively rotating components accessible to the module. This means that no relative rotation can be observed and therefore no dose recording functionality would be possible.

The electronic add-on module may comprise encased within the body or attached thereto an electric power source, e.g. a rechargeable power source. The electric power source may be a battery, for example a coin cell. The electronic add-on module may also comprise a circuit board assembly which is electrically connected to the electric power source. The circuit board assembly may comprise a printed circuit board assembly (PCBA). The circuit board assembly may comprise a substrate equipped with electronic components.

Electronic components may be integrated circuits, processors, conductors, wireless modules or the like. The electronic components may be electrically connected to the circuit board assembly and may therefore also be supplied by power of the electric power source. A circuit board assembly may be configured to receive, transmit, process and/or store data, especially data related to a medicament, to a condition of the drug delivery device and/or to an amount of medicament selected or dispensed. Still further, the electronic add-on module may comprise a sensor arrangement electrically connected to the circuit board assembly.

According to an independent aspect of the present disclosure, the electronic add-on module further comprises a tube which is configured to be permanently rotationally constrained to the body and which is configured to be axially displaceable relative to the body. At least in a dialing mode of the module, the dial is configured to be rotatable relative to the tube. In other words, the tube may serve as a telescoping rotational reference to the stationary components of the pen injector. This allows using the module not only with drug delivery devices having an axially stationary device dial grip but also with drug delivery devices having a so-called dial extension, i.e. injection pens having a device dial grip which moves axially or on a helical path during dose setting and typically also during dispensing. Thus, the provision of the tube allows use of the module for a larger variety of different drug delivery devices while maintaining the above mentioned benefits of referencing the rotation-al measurement of the system relative to the stationary device housing.

In the electronic add-on module the body and the tube may each comprise mating splines configured to permanently rotationally constrain the tube to the body and to permit axial displacement of the tube relative to the body. In an example, the body may be generally tubular in shape and axially long enough to remain engaged with the tube as the tube extends as the device dial grip extends as the dose dial increases. The body is releasably attached to the device housing when the user fits the module to the injection pen. When it is attached the body does not move relative to the device housing until the module is removed from the injection pen. The tube is non rotatable relative to the body but is allowed to move relative to the body in an axial direction. The mating and engaging splines of the body and the tube, respectively, prevent relative rotation of the tube and body and never disengage, so these two components therefore never rotate relative to each other. Further, the tube may be axially constrained to the coupler and/or to the dial, e.g. by means of clips, hooks, beads or the like. This ensures that the tube is entrained if the coupler and/or to the dial moves axially. At least in the dialing mode, the coupler is rotatable relative to the tube.

In order to detect relative movements within the drug delivery device which are indicative of a dose dialing event or a dose dispensing event, the electronic add-on module comprises the sensor arrangement which is provided with at least one non-contact sensor. The sensor arrangement may comprise one or more of an optical sensor, a magnetic sensor, a capacitive sensor and a mechanical sensor. In example of the present disclosure, the non-contact sensor of the electronic add-on module is at least one optical sensor. The sensor arrangement may include a two optical sensor system, e.g. with quadrature implementation, or an optical flow sensor. A reflective type sensor may be used together with regions of reflectivity and absorption present on the target component(s). In more detail, the coupler, e.g. a circumferential portion thereof, and/or the tube, e.g. a proximally facing area thereof, may comprise regions of reflectivity and regions of absorption as encoder regions wherein the at least one optical sensor is configured and arranged to sense the regions of reflectivity. More specifically, a series of first encoder flag segments may be made from black material and a series of second encoder flag segments may be made from white material. Additionally, or alternatively, the encoder flag segments may comprise different surface finishes to increase or decrease reflectivity. The encoder flag segments may for example be twin-shot molded.

The electronic add-on module may comprise a dose recording system for use with a drug delivery device suitable for recording doses that are delivered from the drug delivery device. The electronic add-on module may comprise an electrical power supply, e.g. a battery, like a coin cell type battery, a memory for storing data, a processor configured to control operation of the electronic add-on module and coupled to the electrical power supply and to the memory. In addition, the electronic add-on module may comprise at least two optical sensor units, e.g. a first light source with a corresponding first optical sensor and a second light source with a corresponding second optical sensor, which are in communication with the processor. The optical sensors may be suitable for detecting a movement of an encoder of the drug delivery device, especially different flag segments of an encoder ring, wherein the movement is indicative of doses that are dialed (i.e. selected) and/or delivered from the drug delivery device. There are several different ways suitable to implement the optical sensor units. For example, the optical sensor unit(s) may comprise a radiation detector comprising an electromagnetic radiation emitter, e.g. an LED, like an IR-LED, e.g. an NIR-LED, and a radiation detector.

In one example, the encoder and the optical sensor units are in a quadrature arrangement, i.e. they are a quarter wave out of phase, which means that if both light sources simultaneously emit light, only one sensor changes state for each unit dispensed. For example, this is achieved by providing two optical sensors circumferentially offset by $n*30°+15°$ with n being an integer number. As the encoder and the sensor units are moved relative to each other, one of the optical sensors which previously received the light now does not receive the emitted light or vice versa. This may be achieved by the encoder selectively reflecting light. For example, some flag segments may reflect light, whereas other flag segments may absorb light. As an alternative, the encoder may selectively block light. In other examples the encoder and the optical sensor units may be in anti-phase arrangement. In a still further alternative, the encoder and the optical sensor units are not in an anti-phase arrangement, such that if both light sources simultaneously emit light, none or only one or all optical sensors detect the light depending on the relative position of the encoder.

Examples for the sensor arrangement and the respective working principles suitable for the electronic add-on module are described for example in WO 2019/101962 A1, WO 2023/046787 A1 and WO 2023/099514 A1. Other sensor arrangements including an optical sensor, a magnetic sensor, a capacitive sensor and a mechanical sensor are also suitable for the electronic add-on module of the present disclosure.

The body and/or the tube may be optically transparent as they cover the user read dose window of the pen injector and may also cover part of or all of the drug information label of the pen injector. It would be also possible to have cut through windows to allow the dose window and critical areas of the drug label to be viewed. In addition or as an alternative, it may be required for the light to pass through a transparent region of the dial and to be reflected from target surfaces, e.g. on the proximal end of the tube. Thus, at least a portion of the body, the tube and/or the dial is made from an optically transparent or translucent material.

Further, the electronic add-on module may comprise a clutch element which has clutch features, for example two sets of mating clutch teeth which may each be arranged as a ring of teeth. The coupler may be such a clutch element which is configured such that it cannot rotate relative to the dial of the module, when in one axial position, e.g. when in the dispensing mode, and is allowed to rotate relative to the dial of the module in a second axial position, e.g. when in the dialing mode. In an example a first clutch is provided for rotationally coupling and decoupling the coupler and the dial, wherein the electronic add-on module is configured to be switched between the dialing mode in which the dial is rotationally con-strained to the coupler and the dispensing mode in which the dial is rotationally decoupled from the coupler. The electronic add-on module may be configured to be switched from the dialing mode into the dispensing mode by means of a distal axial displacement of the dial towards the body. Vice versa, the electronic add-on module may be configured to be switched from the dispensing mode into the dialing mode by means of a proximal axial displacement of the dial away from the body.

In some configurations of the electronic add-on module it may be possible for a user to misuse and mislead this system by applying rotation to the dial during dispense. This can lead to dose recording errors as then the rotation of the dial might not equal the rotation of pen injector mechanism. This misuse case can be overcome with the addition of an additional second clutch between the dial and the tube. Such a second clutch may be rotationally free during dialing and rotationally engaged during dispensing in a similar but opposite sense to the first clutch. The optional second clutch is preferably suitable for rotationally coupling and decoupling the tube and the dial, wherein, in the dispensing mode of the electronic add-on module, the tube and the dial are rotationally constrained.

The electronic add-on module may further comprise a separate button arranged at the proximal end of the dial and guided therein such that button is rotatable with respect to the dial. In other words, the button may be attached axially to the dial, but is allowed to rotate relative to it. The button may be designed to have a small contact diameter for its thrust bearing connection to the dial, e.g. as a small diameter pin. Dose dispensing may be initiated through axial pressure on the button. That pressure causes the button, dial and the pen injector button to travel axially, allowing the pen injector to change state. During dispensing the dial may rotate relative to the button which is restrained from rotating by the user's thumb or finger pressing thereon. In an alternative example, the electronic add-on module does not have a separate button. Rather, the dial may be a combined dial button with a proximal actuation end face.

The electronic add-on module may be releasably attached to the drug delivery device by fastening means for releasable attachment, for example, interacting mechanical coupling elements or by frictional or elastic engagement. In order to attach the electronic add-on module on a drug delivery device the body may comprise on its inner side at least one elastomeric grip and/or at least one mechanical clip configured to be releasably attached to the device housing. In a similar manner, the coupler may comprise on its inner side at least one elastomeric grip and/or at least one mechanical clip configured to be releasably attached to the device dial grip. Typically, it is desirable that the body and the coupler do not move relative to the device housing and device dial grip, respectively, until the module is removed from the injection pen.

Generally, the electronic add-on module and especially its circuit board assembly and the sensor arrangement are adapted and configured to detect or calculate a dose set by a user in the dialing mode, a dialing start point, a dialing end point, a dispensing start point, a dialing end point and/or a dose amount ejected from the drug delivery device in the dispensing mode. In an example, the sensor may monitor the rotation of the dial relative to the tube. It may also monitor the rotation of the dial relative to the coupler. The sensor may read either or both of these relative rotations and it may consist of one or more individual sensors in order to read these multiple motions.

In more detail, the electronic add-on module could operate in one of three ways: In a first operation mode, the sensor may only have a sensing direction to monitor the relative rotation of the dial and the tube. These components rotate relative to each other during dialing. This would then operate in a dial encoding sense where the module would count the dose being dialed, it may then use information from an optional switch to identify when the dose was dispensed and convert the dialed count into a dose count. In a second operation mode, if the dial rotates relative to the coupler during dispensing, e.g. if the first clutch is disengaged, the sensor may only have a sensing direction to monitor the relative rotation of the dial and the coupler, i.e. to count dose dispense information. This allows the module is directly count and record dose dispensed. In a third operation mode, the sensor may have both above mentioned sensing directions and can therefore count dose dialed information and dose dispensed information The addition of the dose dispensed information allows the module to account for edge use cases where the user stops dispensing mid-dose. Without the dose dispensed information, and where the sensor system is incremental or partially absolute but not fully absolute, it would not be possible for the module to know how much of the dose had been dispensed and might have to assume it had been fully dispensed.

Still further, the electronic add-on module may comprise a switch electrically connected to the electric power source and/or the circuit board assembly wherein the switch may be configured to be operated when the electronic add-on module is switched from the dialing mode into the dispensing mode. The switch, e.g. a microswitch, may be configured to be actuated to activate electronic functionalities of the electronic add-on module. For example, the switch may be used to activate the sensor arrangement. Consequently, detection by the sensor arrangement may only be conducted, when the sensor arrangement is activated. Therefore, the switch may allow to reduce power consumption of electronics. In addition, the switch may prevent that signals are detected accidentally although the electronic add-on module is not used. Further, an axial relative movement of the dial and/or the button in the distal direction along the longitudinal axis with respect to the body may actuate the switch. When the electronic add-on module is releasably attached to a drug delivery device, this relative axial movement may further be used to press a dose button of the drug delivery device, wherein pressing the dose button may cause or initiate a dose to be dispensed. Consequently, the switch may only be actuated, when a dose is dispensed. If the electronic module has other sensors or electronic components in addition to the sensor arrangement, such as a display, these components may be activated or deactivated independently of the switch, for example by a second switch.

The electronic add-on module may be an electronic dose recording system for determining, storing and/or transmitting data indicative of at least a condition of the drug delivery device or its use. For example, the system may detect if the drug delivery device is switched be-tween a dose setting mode and a dose dispensing mode and vice versa. In addition or as an alternative, the system may detect if a dose is set and/or if a dose is dispensed. Still further, the system may detect the amount of dose selected and/or the amount of dose dispensed. Preferably, the electronic add-on module is configured such that it may be switched from a first state having lower energy consumption into a second state having higher energy consumption. This may be achieved by operation of the electronic add-on module, especially by actuating the microswitch. The first state may be a sleeping mode and the second mode may be a detection and/or communication mode. As an alternative, an electronic control unit may issue a command, e.g. a signal, to another unit of the electronic dose recording system such that this unit is switched on or rendered operational.

The electronic add-on module may further comprise a communication unit for communicating with another device, e.g. a wireless communications interface for communicating with another device via a wireless network such as Wi-Fi or Bluetooth, or even an interface for a wired communications link, such as a socket for receiving a Universal Series Bus (USB), mini-USB or micro-USB connector. Preferably, the electronic add-on module comprises an RF, Wi-Fi and/or Bluetooth unit as the communication unit. The communication unit may be provided as a communication interface between the electronic add-on module and the exterior, such as other electronic devices, e.g. mobile phones, personal computers, laptops and so on. For example, dose data may be transmitted by the communication unit to the external device. The dose data may be used for a dose log or dose history established in the external device.

Although not specifically mentioned above, one or more of the component parts of the electronic add-on module may be a sub-assembly consisting of two or more separate parts attached to each other during manufacture of the module and/or during attachment to the drug delivery device.

In a further aspect, the disclosure describes an assembly comprising a drug delivery device and an electronic add-on module according to the aforementioned aspects. The electronic add-on module may be releasably attached to the drug delivery device. In more detail, the drug delivery device comprises a device housing and a device dial grip which is rotatable relative to the device housing for setting a dose, wherein the body of the electronic add-on module is releasably attached to the device housing and wherein the coupler of the electronic add-on module is releasably attached to the device dial grip. The drug delivery device may for example be the drug delivery device known from EP 3 164 173 A1. Other suitable working principles of drug delivery devices to be used may for example be de-scribed in EP 1 570 876 B1, EP 2 814 547B1, EP 2 890 434 B1, WO 2005/018721 A1, WO 2009/132777 A1, WO 2014/033195 A1, U.S. Pat. Nos. 5,693,027 A, 6,663,602 B2, 7,241,278 B2 or U.S. Pat. No. 9,937,294 B2.

If the drug delivery device has a similar working principle as in the example of WO 2004/078239 A1, during dose setting components of the drug delivery device may perform the following movements. A housing may be stationary and may be used as a reference system for the further movements of other components. A plunger may be stationary and may be guided in a housing thread. A drive sleeve may perform a helical movement, i.e. a combined axial and rotational movement, and may be in threaded engagement with the plunger. A dial grip may perform a helical movement. A dose button may be free to rotate but axially constrained to the drive sleeve. For example, the dose button may be axially retained to the drive sleeve by a clutch. An optional clutch may perform a helical movement and may couple a number sleeve to the drive sleeve. An optional clutch spring may perform an axial movement and may be guided in housing splines and may click over clutch teeth. An optional number sleeve may be permanently fixed on the dial grip and may perform a helical movement and may be guided in a housing thread. An optional last dose nut may perform a helical movement on a drive sleeve track of the drive sleeve and may be rotationally constrained to the housing. Hence, the last dose nut may perform axial movement relative to the housing and a helical movement with respect to the drive sleeve.

During dose dispensing components of the drug delivery device may perform the following movements. The housing may remain stationary as a reference system for the further movements of other components. The plunger may perform a helical movement and may be guided in the housing thread. The drive sleeve may perform a pure axial movement and may be in threaded engagement with the plunger. The dose dial grip may perform a helical movement and may be permanently fixed on the number sleeve. The dose button may perform an axial movement if coupled to the drive sleeve and/or the clutch. The optional clutch may perform pure axial movement and may de-couple the number sleeve from the drive sleeve. The optional clutch spring may perform pure axial movement and may be rotationally constrained to the clutch due to a pressure applied to the dose button. The optional number sleeve may perform a helical movement and may be guided in the housing thread. The optional last dose nut may maintain its axial position on the drive sleeve track and may be rotationally constrained to the housing.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liset 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including noncodeable amino acids, or amino acids, including noncodeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victo-za®), Semaglutide, Taspoglutide, Albiglutide (Syncria®), Dulaglutide (Trulicity®), rExendin-4, CJC-1134-PC, PB-1023, TTP-054, Langlenatide/HM-11260C (Efpeglenatide), HM-15211, CM-3, GLP-1 Eligen, ORMD-0901, NN-9423, NN-9709, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, ZP-DI-70, TT-401 (Pegapamodtide), BHM-034. MOD-6030, CAM-2036, DA-15864, ARI-2651, ARI-2255, Tirzepatide (LY3298176), Bamadutide (SAR425899), Exenatide-XTEN and Glucagon-Xten.

An example of an oligonucleotide is, for example: mipomersen sodium (Kynamro®), a cholesterol-reducing antisense therapeutic for the treatment of familial hypercholesterolemia or RG012 for the treatment of Alport syndrom.

Examples of DPP4 inhibitors are Linagliptin, Vildagliptin, Sitagliptin, Denagliptin, Saxagliptin, Berberine.

Examples of hormones include hypophysis hormones or hypothalamus hormones or regulatory active peptides and their antagonists, such as Gonadotropin (Follitropin, Lutropin, Choriongonadotropin, Menotropin), Somatropin (Somatropin), Desmopressin, Terlipressin, Gonadorelin, Triptorelin, Leuprorelin, Buse Relin, Nafarelin, and Goserelin.

Examples of polysaccharides include a glycosaminoglycan, a hyaluronic acid, a heparin, a low molecular weight heparin or an ultra-low molecular weight heparin or a derivative there-of, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof.

Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present invention include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, small modular immunopharmaceuticals (SMIP), binding-domain immunoglobulin fusion proteins, camelized antibodies, and immunoglobulin single variable domains. Additional examples of antigen-binding antibody fragments are known in the art.

The term "immunoglobulin single variable domain" (ISV), interchangeably used with "single variable domain", defines immunoglobulin molecules wherein the antigen binding site is present on, and formed by, a single immunoglobulin domain. As such, immunoglobulin single variable domains are capable of specifically binding to an epitope of the antigen without pairing with an additional immunoglobulin variable domain. The binding site of an immunoglobulin single variable domain is formed by a single heavy chain variable domain (VH domain or VHH domain) or a single light chain variable domain (VL domain). Hence, the antigen binding site of an immunoglobulin single variable domain is formed by no more than three CDRs.

An immunoglobulin single variable domain (ISV) can be a heavy chain ISV, such as a VH (derived from a conventional four-chain antibody), or VHH (derived from a heavy-chain antibody), including a camelized VH or humanized VHH. For example, the immunoglobulin single variable domain may be a (single) domain antibody, a "dAb" or dAb or a Nanobody® ISV (such as a VHH, including a humanized VHH or camelized VH) or a suitable fragment thereof. [Note: Nanobody® is a registered trademark of Ablynx N.V.]; other single variable domains, or any suitable fragment of any one thereof.

"VHH domains", also known as VHHs, VHH antibody fragments, and VHH antibodies, have originally been described as the antigen binding immunoglobulin variable domain of "heavy chain antibodies" (i.e., of "antibodies devoid of light chains"; Hamers-Casterman et al. 1993 (Nature 363: 446-448). The term "VHH domain" has been chosen in order to distinguish these variable domains from the heavy chain variable domains that are present in conventional 4-chain antibodies (which are referred to herein as "VH domains") and from the light chain variable domains that are present in conventional 4-chain antibodies (which are referred to herein as "VL domains"). For a further description of VHH's, reference is made to the review article by Muyldermans 2001 (Reviews in Molecular Biotechnology 74: 277-302).

For the term "dAb's" and "domain antibody", reference is for example made to Ward et al. 1989 (Nature 341: 544), to Holt et al. 2003 (Trends Biotechnol. 21: 484); as well as to WO 2004/068820, WO 2006/030220, WO 2006/003388. It should also be noted that, although less preferred in the context of the present invention because they are not of mammalian origin, single variable domains can be derived from certain species of shark (for example, the so-called "IgNAR domains", see for example WO 2005/18629).

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

An example drug delivery device may involve a needle-based injection system as described in Table 1 of section 5.2 of ISO 11608-1:2014(E). As described in ISO 11608-1:2014 (E), needle-based injection systems may be broadly distinguished into multi-dose container systems and single-dose (with partial or full evacuation) container systems. The container may be a replaceable container or an integrated non-replaceable container.

As further described in ISO 11608-1:2014(E), a multi-dose container system may involve a needle-based injection device with a replaceable container. In such a system, each container holds multiple doses, the size of which may be fixed or variable (pre-set by the user). Another multi-dose container system may involve a needle-based injection device with an integrated non-replaceable container. In such a system, each container holds multiple doses, the size of which may be fixed or variable (pre-set by the user).

As further described in ISO 11608-1:2014(E), a single-dose container system may involve a needle-based injection device with a replaceable container. In one example for such a system, each container holds a single dose, whereby the entire deliverable volume is expelled (full evacuation). In a further example, each container holds a single dose, whereby a portion of the deliverable volume is expelled (partial evacuation). As also described in ISO 11608-1:2014 (E), a single-dose container system may involve a needle-based injection device with an integrated non-replaceable container. In one example for such a system, each container holds a single dose, whereby the entire deliverable volume is expelled (full evacuation). In a further example, each container holds a single dose, whereby a portion of the deliverable volume is expelled (partial evacuation).

The terms "axial", "radial", or "circumferential" as used herein may be used with respect to a longitudinal axis of the electronic add-on module, the first portion, the second portion, the drug delivery device, the cartridge, the housing, the cartridge holder or the assembly of the drug delivery device and the electronic add-on module, e.g. the axis which extends through the proximal and distal ends of the cartridge.

"Distal" is used herein to specify directions, ends or surfaces which are arranged or are to be arranged to face or point towards dispensing end of the drug delivery device if connected with the electronic add-on module and/or point away from, are to be arranged to face away from or face away from the proximal end. The dispensing end may be the needle end where a needle unit is or is to be mounted to the device, for example. On the other hand, "proximal" is used to specify directions, ends or surfaces which are arranged or are to be arranged to face away from or point away from the dispensing end and/or from the distal end of the electronic add-on module or the drug delivery device or components thereof. Furthermore, when the electronic add-on module is considered alone, the term "distal" may be used with regard to the more distal end of the electronic add-on module, which is located closer to the dispensing end of the drug delivery device when attached to the drug delivery device, and the term "proximal" may be used with regard to the proximal end of the electronic add-on module, which is located further away from the dispensing end of the drug delivery device when attached to the drug delivery device.

In the following, non-limiting, examples of the electronic add-on module, the drug delivery device and the assembly of the drug delivery device and the electronic add-on module are described in more detail by making reference to the drawings, in which:

BRIEF DESCRIPTION OF THE FIGURES

FIG. 1 shows an exploded view of an electronic add-on module according to a first embodiment and the proximal end of a drug delivery device;

FIG. 2 shows a sectional view of the module of FIG. 1;

FIG. 3 shows a detail of FIG. 2;

FIG. 18 shows an exploded view of an electronic add-on module according to a fifth embodiment;

FIG. 19 shows an exploded view of components of the module of FIG. 18 from the opposite side;

FIG. 20 shows a component of the module of FIG. 18;

FIG. 21 a sectional view of the module of FIG. 18 in the dialing mode;

FIG. 22 a sectional view of the module of FIG. 18 in the dispensing mode;

DETAILED DESCRIPTION

Figure 4:
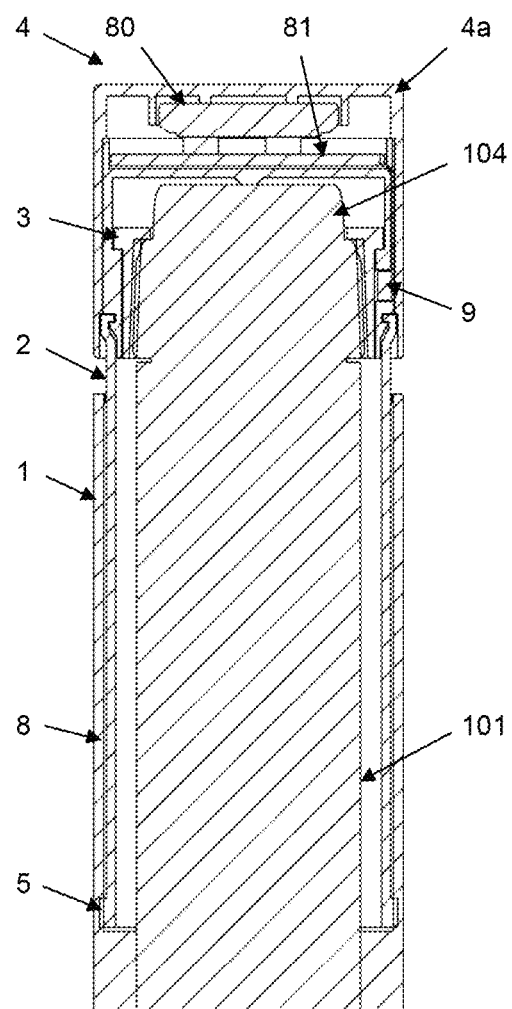
FIG. 4 a sectional view of the module of FIG. 1 in the dialing mode.

FIG. 1 shows an exploded view of an exemplary electronic add-on module which may be attached on a drug delivery device 100 which is depicted in FIG. 1 only partially, namely only its proximal end. The module extends from a distal point (lower end in FIG. 1) to a proximal direction or from a proximal point (upper end in FIG. 1) to a distal direction along a longitudinal axis I and may be fitted onto the drug delivery device 100 such that the axis I of the module is aligned concentrically with the drug delivery device axis II.

The drug delivery device 100 is a pen-type injector comprising a device housing 101 in which a drive mechanism for dose setting and dose dispensing is arranged (not shown in detail). The set dose may be displayed via the dosage window 102. In order to set or dial a dose for delivery a user may rotate or dial a device dial grip 103 with respect to the housing 101, which device dial grip 103 is arranged at or near a proximal end of the housing 101. Depending on the type of drive mechanism for dose setting and dose dispensing, during dose setting the dos device e dial grip 103 may either perform a helical movement, i.e. a combined axial and rotational movement, or may perform pure rotational movement.

The drive mechanism of the drug delivery device 100 may comprise a plunger, a drive sleeve, a clutch, a clutch spring, a number sleeve, a last dose nut and so on, which may move during dose setting and/or dose dispensing. Although not all of these components are shown in detail, for example, the drive mechanisms disclosed in EP 1 570 876, EP 2 814 547, U.S. Pat. No. 9,937,294 B2 or WO 2004/078239 A1 represent suitable drive mechanisms for the present disclosure. However, other drive mechanisms are also applicable.

Once the dose is set by means of the device dial grip 103, the user may press a dose button 104 arranged at the proximal end of the drug delivery device 100 in the distal direction in order to dispense the dose. When pressing the dose button 104, the user applies a force on a proximal end surface of the dose button 104 directed towards the proximal end of the drug delivery device 100. The force moves the dose button 104 in the distal direction of the pen and parallel to the longitudinal axis II. This axial movement of the dose button 104 releases the drive mechanism for example by de-coupling a number sleeve from the drive sleeve, wherein irrespective of which component of the drug delivery device 100 performs a rotational movement during dose delivery, the dose dial grip 103 is coupled to a respective component in order to perform a rotational movement during dose delivery.

In order for an electronic add-on module to be functionally attached to a drug delivery device 100, i.e. attached and usable, either the drug delivery device 100 can be adapted to the electronic add-on module or, conversely, the electronic add-on module can be adapted to the drug delivery device 100. In this regard, the electronic add-on module may comprise a coupling portion.

In the following, different embodiments of an electronic add-on module of the present disclosure are described in more detail with reference to a drug delivery device as partially depicted in FIG. 1. However, it will be understood that the module may be fitted on a variety of different types of drug delivery devices, e.g. devices with a dial extension and devices without a dial extension or devices with a separate dose button 104 or devices with a combined dose button/dial grip component. For this reason, the drug delivery device 100 is depicted in the sectional views as one solid body without representing the details of the device housing 101, the device dial grip 103, the device dose button 104 or the further components of the drive mechanism.

Embodiment 1

An exploded view of the relatively moveable elements of the electronic module are shown in FIG. 1. The module comprises substantially four components, namely a body 1, a tube 2, a coupler 3 and a dial 4. These four components may be subassemblies comprising two or more components or may house or retain further components.

The body 1 is largely tubular in shape and is axially long enough to remain engaged with the tube 2 when the tube 2 extends as the device dial grip 103 extends as the dose dial increases. The body 1 is releasably attached to the device housing 101 of the drug delivery device when the user fits the module to the drug delivery device 100. When it is attached the body 1 does not move relative to the device housing 101 until the module is removed from the drug delivery device 100. The means of releasable attachment is not depicted in detail, but may comprise an elastomeric grip, mechanical clip features or other such features.

The tube 2 is non rotatable relative to the body 1 but is allowed to move relative to the body 1 in an axial direction along axis I. A spline feature 5 and a corresponding spline feature 8 prevent relative rotation of the tube 2 and body 1 and never disengage when the module is fitted onto the drug delivery device 100, so the two components 1, 2 therefore never rotate relative to each other.

The coupler 3 is releasably attached to the device dial grip 103 of the drug delivery device 100 when the user fits the module to the drug delivery device. When it is attached the coupler 3 does not move relative to the device dial grip 103 until the module is removed from the drug delivery device. The means of releasable attachment is not depicted in detail, but may comprise an elastomeric grip, mechanical clip features or other such features. The coupler 3 has clutch features 6 in the form of a ring of teeth such that it cannot rotate relative to the dial 4 of the module, when in one axial position and is allowed to rotate relative in a second axial position.

It can be seen further from FIGS. 3 and 4 that the coupler 3 is retained concentrically within the dial 4 of the module. The dial 4 has corresponding clutch features 7 in the form of a ring of teeth to engage with the coupler 3. Clutch features 6 of the coupler 3 and clutch features 7 of the dial 4 together form a first clutch for rotationally coupling or decoupling the coupler 3 and the dial 4.

It can also be seen from FIG. 2 that the dial 4 comprises an outer shell 4a which may be opaque and an insert 4b which may be transparent and is retained and permanently fixed therein. The tube 2 comprises at its proximal end a radially inwardly protruding flange which is retained by corresponding features of the insert 4b of the dial 4 such that it can rotate relative to the dial 4 but is prevented from relative axial movement with respect to the dial 4. As can be seen from FIGS. 2 and 3 the tube 2 is attached to the coupler 3 via the dial insert 4b, such that the tube 2 may perform a limited axial movement together with the dial 4 relative to the coupler 3.

The body 1 and the tube 2 as embodied here are intended to be optically transparent as they cover the user read device dose window 102 of the drug delivery device 100 and may also cover part of or all of the drug information label of the drug delivery device 100. It would be also possible to have cut through windows in the body 1 and/or the tube 2 to allow the device dose window 102 and critical areas of the drug label to be viewed, these are not shown in the Figures.

A close up view of a cross section through the dial 4 is shown in FIG. 3. In this view a sensor arrangement 9 is visible. The sensor arrangement 9 is fixed in the dial 4, specifically in the insert 4b. As can be seen further in the close up view in FIG. 4 the sensor arrangement 9 may monitor the rotation of the dial 4 relative to the tube 2. The tube 2 has on its proximally facing end surface a pattern of regions of reflectivity 10 and regions of absorption forming a disc-shaped encoder ring visible through the transparent insert 4b. The sensor arrangement 9 may comprise at least one optical sensor at its distal end in order to detect the regions of reflectivity 10 upon relative rotation between the tube 2 and the dial 4. The sensor arrangement 9 may also monitor the rotation of the dial 4 relative to the coupler 3. The coupler 3 has on its lateral surface a pattern of regions of reflectivity 11 and regions of absorption forming a cylindrical encoder ring visible through the transparent insert 4b. The sensor arrangement 9 may comprise at least one optical sensor at its radially inner face in order to detect the regions of reflectivity 11 upon relative rotation between the coupler 3 and the dial 4. The sensor arrangement 9 may read either or both of these relative rotations and it may consist of one or individual sensors in order to read these multiple motions.

Generally, the sensor arrangement 9 may be of any technological type, but may be preferentially non-contact and further preferentially optical as explained in the above example. The sensor arrangement 9 may be of any suitable technology including but not limited to a two optical sensor system, e.g. with quadrature implementation, or an optical flow sensor. A reflective type sensor arrangement 9 is one suitable example with regions of reflectivity 10, 11 and regions of absorption present on the target component(s) 2, 3.

Figure 5:
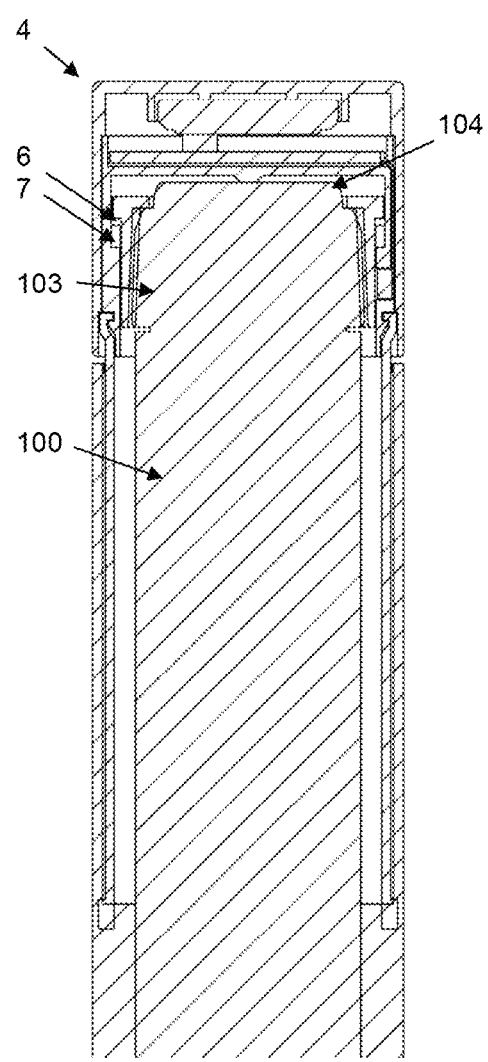
FIG. 5 a sectional view of the module of FIG. 1 in the dispensing mode.
Figure 6:
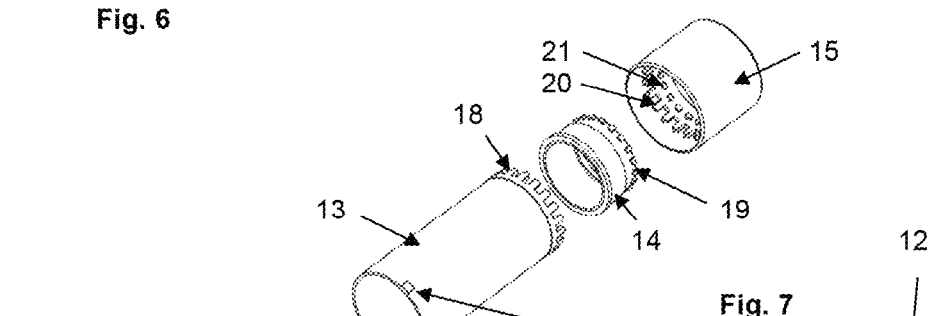
FIG. 6 shows an exploded view of an electronic add-on module according to a second embodiment.
Figure 7:
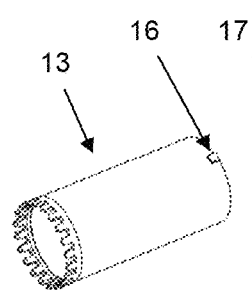
FIG. 7 shows an exploded view of two components of the module of FIG. 6 from the opposite side.

FIGS. 4 and 5 show the module and a schematic portion of the drug delivery device 100 in a dialing mode or state (FIG. 4) where no distal pressure is applied to the dial 4 and the device dose button 104 is not depressed and in a dispensing mode or state (FIG. 5) where distal pressure is applied to the dial 4 and the device dose button 104 is depressed axially to initiate and maintain dispense. In this dispensing mode or state it can be seen that the dial 4 has moved distally relative to the coupler 3 and the two sets of clutch features 6 and 7 have separated allowing relative rotation. Therefore, the dial 4 is rotationally coupled to the device dial grip 103 during 'dialing', i.e. in the dialing mode or state (FIG. 4), and is rotationally un-coupled during 'dispensing' in the dispensing mode or state (FIG. 5).

The dial 4 is operable by a user in the dialing mode by rotating the outer shell 4a relative to the body 1. This rotation entrains the coupler 3 due to the engaged clutch features 6, 7 and this in turn entrains the device dial grip 103. Thus, a dose may be set in the drug delivery device 100 by rotating the dial 4 when the module is attached to the drug delivery device 100 as depicted. In addition, the dial 4 is operable by a user to switch from the dialing mode into the dispensing mode by pressing on the proximal face of the outer shell 4a relative to the body 1. This causes an axial movement of the dial 4 relative to the coupler 3 such that clutch features 6, 7 disengage. Simultaneously, the device dose button 104 is depressed due to the contact with the insert 4b which switches the drive mechanism within the drug delivery device 100 into a dispensing mode, too. Applying further pressure on the dial 4 in the distal direction will move the dial 4 which may have been retracted from the body 1 during a dose dialing operation (not depicted) back towards the body 1, i.e. the tube 2 slides back into the body 1. This axial movement entrains the device dose button 104 which cause ejection of the set dose from the drug delivery device 100.

The module could operate in one of three ways. In a first operation mode, the sensor arrangement 9 only has a sensing direction towards the regions of reflectivity 10 on the proximal end of the tube 2 and can therefore monitor the relative rotation of the dial 4 and the tube 2. These components rotate relative to each other during dialing. This would then operate in a 'dial encoding' sense where the module would count the dose being dialed, it would then use information from an optional switch (not shown) to identify when the dose was dispensed and convert the dialed count into a dose count. Alternatively, in a second operation mode, the sensor arrangement 9 has both sensing directions towards the regions of reflectivity 10 on the proximal end of the tube 2 and towards the regions of reflectivity 11 on the outer side of the coupler 3, and can therefore count dose dialed information and dose dispensed information. The dial 4 will rotate relative to the coupler 3 during dispensing as the clutch features 6 and 7 disengage. The addition of the dose dispensed information allows the module to account for edge use cases where the user stops dispensing mid-dose. Without the dose dispensed information, and where the sensor system is incremental or partially absolute but not fully absolute, it would not be possible for the module to know how much of the dose had been dispensed and might have to assume it had been fully dispensed. Alternatively, in a third operation mode, the sensor arrangement 9 only has sensing direction towards the regions of reflectivity 11 on the outer side of the coupler 3 and can therefore count dose dispense information only. This allows the module to directly count and record dose dispensed.

It may be apparent from the above description that, if using the third operation mode above, it might be feasible for users to misuse and mislead this system by applying rotation to the dial 4 during dispense. This could lead to dose recording errors as then the rotation of the dial 4 might not equal the rotation of the drug delivery device mechanism. This misuse case can be overcome with the addition of an additional clutch between the dial 4 and the tube 2. Such a clutch would be rotationally free during dialing and rotationally engaged during dispensing in a similar but opposite sense to the other clutch features 6 and 7. Embodiment 2 includes such a further clutch within a slightly different arrangement.

Embodiment 2

Embodiment 2 has a broadly similar arrangement to Embodiment 1. A body 12 releasably attaches to the device housing 101 of the drug delivery device 100, in the same manner as in Embodiment 1. A tube 13 is axially slidable relative to the body 12. The tube 13 is non-rotatable relative to the body 12, due to the engagement of a spline 16 on the outer side of the tube 13 with a spline 17 on the inner side of the body 12. A coupler 14 is releasably attached to the device dial grip 103 in the same manner as in Embodiment 1. A dial 15 has clutch features 20 to clutch features 18 of the tube 13 and also has clutch features 21 to clutch features 19 of the coupler 14. Each of these clutch features may be formed as a respective ring of teeth as depicted. Clutch features 19, 21 form a first clutch and clutch features 18, 20 form a second clutch.

Figure 9:
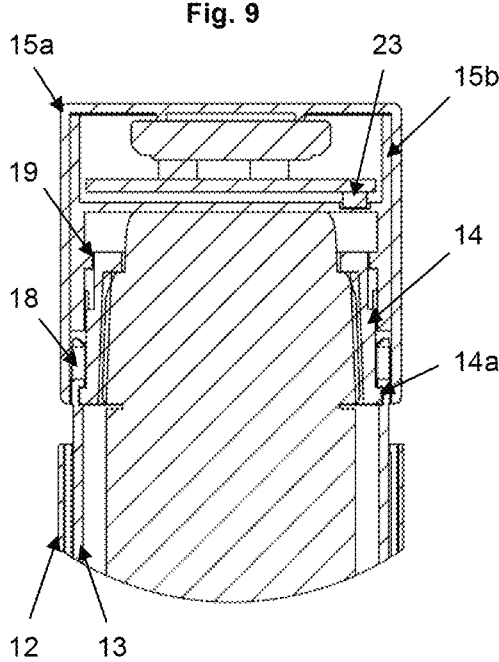
FIG. 9 a sectional view of the module of FIG. 6 in the dialing mode.
Figure 10:
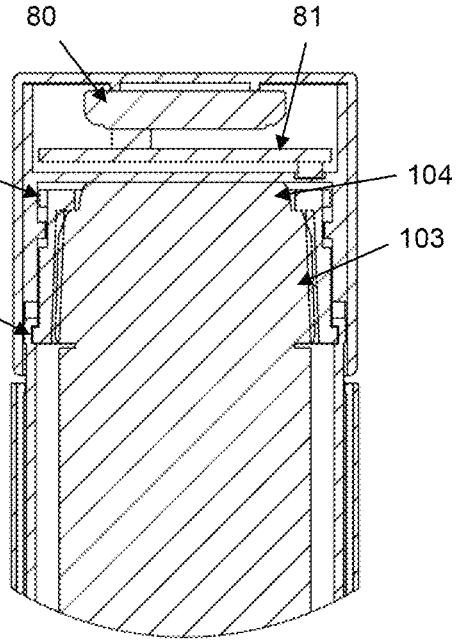
FIG. 10 a sectional view of the module of FIG. 6 in the dispensing mode.

FIGS. 9 and 10 show a partial cross section view of the module and the drug delivery device 100 when in a dialing mode (FIG. 9), i.e. when the device button 104 is not pressed, and when in a dispensing mode (FIG. 10), i.e. when the device button 104 is pressed. In the dialing mode it can be seen that the clutch features 18 and 20 are axially separated are not engaged and therefore relative rotation between the dial 15 and the tube 13 is possible. It can also be seen that the clutch features 19 and 21 are engaged and therefore relative rotation between the dial 15 and the coupler 14 is not permitted. In this state the user can use the dial 15 to rotate the device dial grip 103 of the drug delivery device 100 and dial a desired dose. The act of dialing causes the dial 15 and coupler 14 to rotate with the device dial grip 103 and therefore extend on a helical path. In FIGS. 9 and 10 the features that axially connect the tube 13 to the coupler 14 can also be seen. The tube 13 is fixed near its proximal end with an inner recess 13a to an outer flange 14a of the coupler 14 in an axial direction but is free to rotate. These are effectively axisymmetric based on this cross section therefore, it can be seen that only rotation is allowed between these two components and axial (and radial) motion is blocked. Therefore, during dialing the tube 13 which is stopped from rotating by the body 12 extends only with axial movement.

To initiate a dispense the button portion, i.e. the proximal end face of the dial 15, is pressed as is normal, this state is shown in FIG. 10. The dial 15 has travelled axially a short distance in the distal direction. This has allowed a change in state or mode of both sets of clutch features. The first clutch 19, 21 between the dial 15 and the coupler 14 is now disengaged allowing relative rotation. The second clutch 18, 20 between the dial 15 and the tube 13 is now engaged preventing relative rotation. Therefore, during dispense the coupler 14 is allowed to rotate with the device dial grip 103 whereas the dial 15 is actively prevented from rotating due to its engagement with the tube 13 which in turn is prevented from rotating due to the body 12. Therefore, relative rotation of the coupler 14 and the dial element 15 only occurs during dispensing and the magnitude of the rotation is constrained to be accurately representative of the actual dose dispensed. Therefore, this embodiment seeks to encode this interface.

Figure 8:
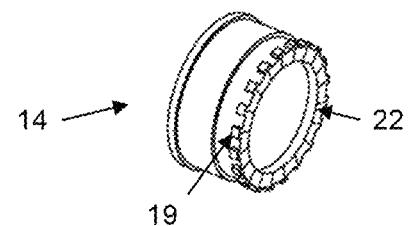
FIG. 8 shows a component of the module of FIG. 6.

In FIG. 8 a view of the coupler 14 is shown. On the proximal surface of the coupler 14 there is an arrangement of reflective surfaces 22 and non-reflective surfaces. A sensor arrangement 23 with an optical sensor is mounted in the dial 15 and can be seen in FIGS. 9 and 10. In the case of the depicted embodiment this may be a reflective optical type sensor which is configured to sense the reflective surfaces 22 of the coupler 14. Other types of sensor technology or sensor arrangements could equally be used to encode the rotation between the two components in accordance with this disclosure.

Embodiment 3

Figure 11:
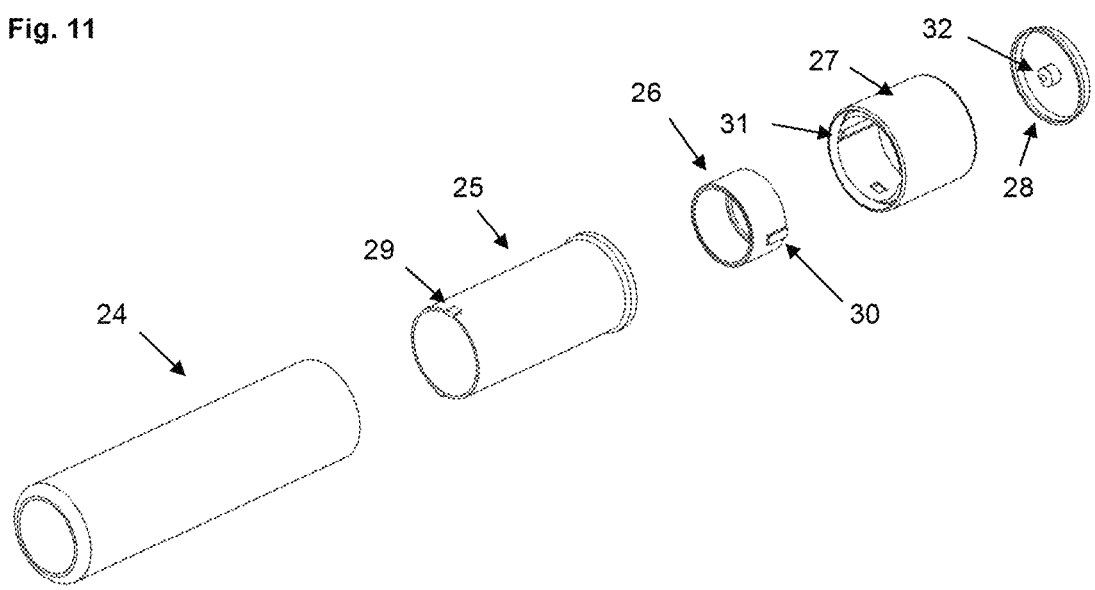
FIG. 11 shows an exploded view of an electronic add-on module according to a third embodiment.
Figure 12:
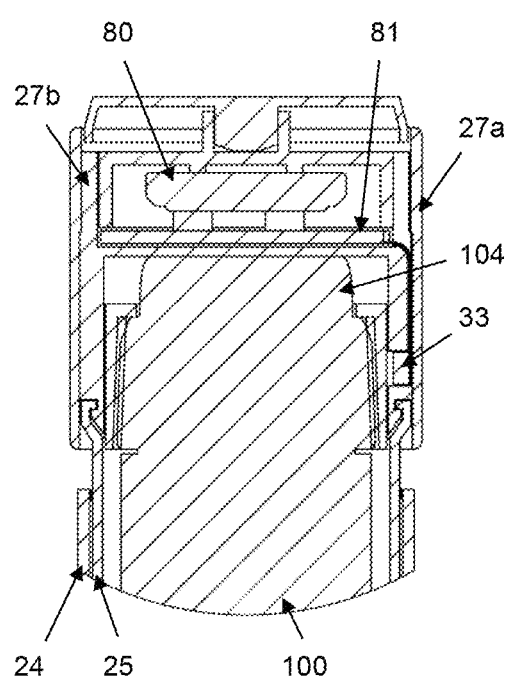
FIG. 12 a sectional view of the module of FIG. 11 in the dialing mode.
Figure 13:
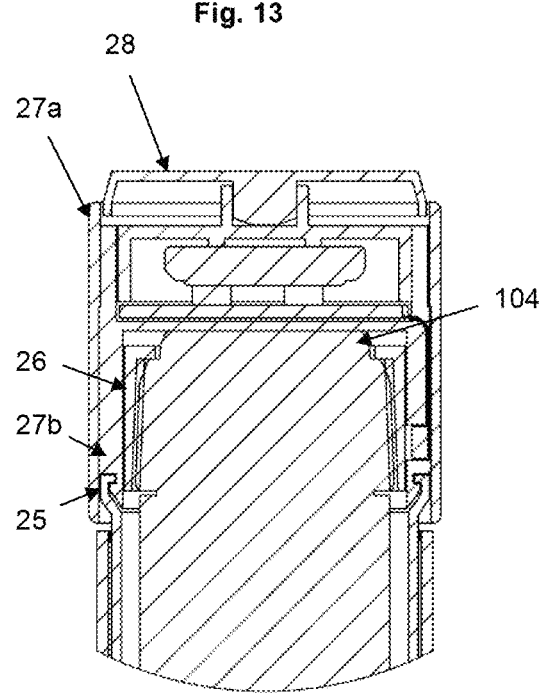
FIG. 13 a sectional view of the module of FIG. 11 in the dispensing mode.
Figure 14:
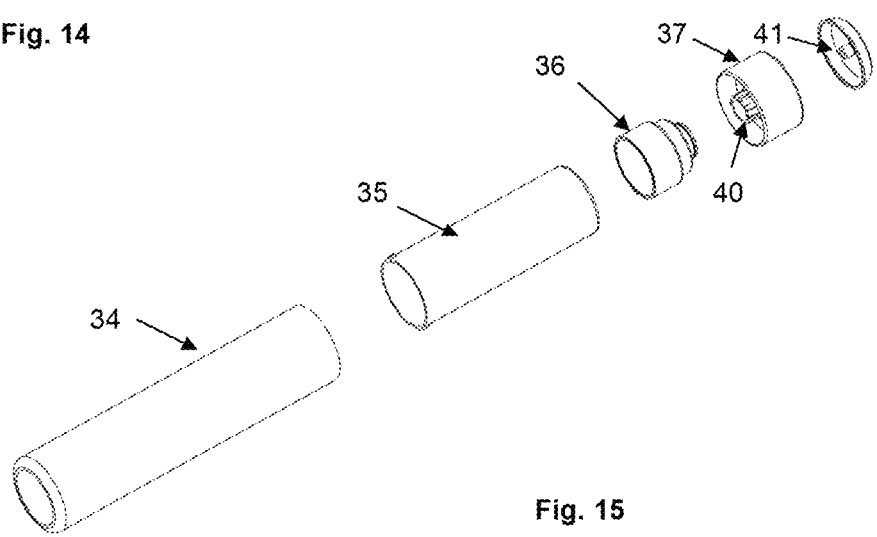
FIG. 14 shows an exploded view of an electronic add-on module according to a fourth embodiment.
Figure 15:
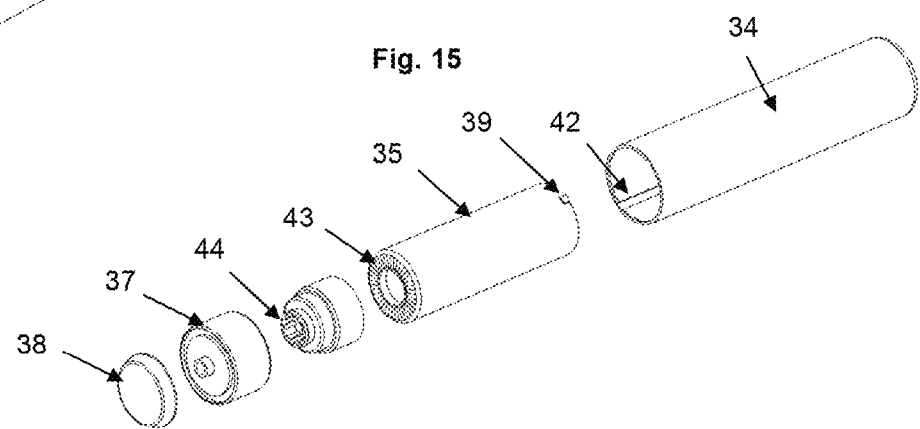
FIG. 15 shows an exploded view of components of the module of FIG. 14 from the opposite side.

The third embodiment is shown in FIGS. 11 to 13. The arrangement consists of similar components to the previous embodiments, a body 24 a tube 25 a coupler 26 and a dial 27 with an outer shell 27 and an insert 27b. The tube 25 is guided in the dial 27, here in its insert 27b, in a similar manner as explained with respect to Embodiment 1. In this embodiment there is an additional button 28. In this embodiment there are no clutch features, all the components remain rotationally constrained in the same way through both the dialing mode and dispensing mode. Similar to previous embodiments the tube 25 is rotationally constrained to the body 24 through spline 29. The body 24 is releasably fixed to the device housing 101 and once fitted is fixed in all degrees of freedom. The coupler 26 is releasably fixed to the drug delivery device dial grip and once fitted is fixed in all degrees of freedom. Both releasable connections are not shown in detail, as all previous embodiments multiple arrangements are possible including friction fits and clip attachment methods.

The coupler 26 is permanently rotationally coupled with the dial 27 but is allowed to trans-late relative to it in the axial direction by means of a protrusion 30 on the outer side of the coupler 26 engaging a longitudinal recess 31 on the inner side of the dial 27. The button 28 is attached axially to the dial 27 but is allowed to rotate relative to it. The button 28 is de-signed to have a small contact diameter for its thrust bearing connection to the dial element 27 this may be illustrated as a small diameter pin 32.

As there are no clutch features that change state or mode in this embodiment, the coupler 26 and the dial 27 always rotate with the device dial grip 103. The tube 25 is always non-rotational relative to the device housing 101. The user dials the dose through the dial 27, then a dose is initiated through axial pressure on the button 28. That pressure causes the button 28, the dial 27 and the device button 104 to travel axially, allowing the drug delivery device 100 to change state to dialing. These two positions are shown in FIGS. 12 and 13. During dispensing the dial 27 rotates therefore the button 28 rotates relative to it as it is restrained from rotating by the user's thumb or finger.

A sensor arrangement 33 is assembled as part of the dial 27. It is configured to read the rotation of the tube 25 relative to the dial element 27. In an example, the sensor arrangement 33 comprises an optical sensor which reads in a distal axial direction, through an optically transparent section of the dial 27 and reads the proximal axial end face of the tube 25. Details are not shown for this end face but suitable alternating regions of reflectivity and non-reflectivity have been shown in previous embodiments. The sensor arrangement 33 could be active in either or both of dialing and dispensing as there is relative rotation across the sensed interface in both operations. In this way it is possible to encoder either or both of dialed doses and dispensed doses.

Embodiment 4

The fourth embodiment is functionally similar to Embodiment 3 with a slightly different mechanical arrangement. FIGS. 14 to 17 show the details of this embodiment. Similar to Embodiment 3 there is a body 34, a tube 35, a coupler 36, a dial 37, and a button 38. Also similar to Embodiment 3 there is a spline 39 on the tube which engages to prevent rotation with a spline 42 on the body 34. Again similar to Embodiment 3 there is a small diameter contact formed on the pin feature 41 between the button 38 and the dial 37. The arrangement for preventing rotation between the coupler 36 and the dial 37 is slightly differently arranged in this embodiment with spline features 40, on the dial 37 engaging with spline features 44 on the coupler 36.

Figure 16:
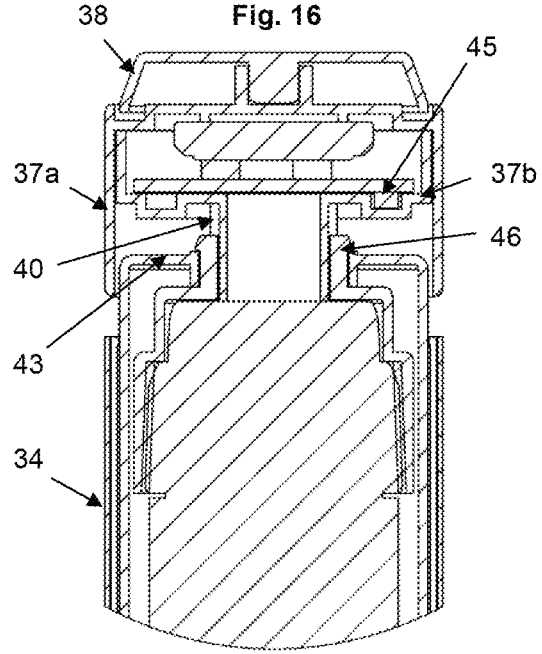
FIG. 16 a sectional view of the module of FIG. 14 in the dialing mode.
Figure 17:
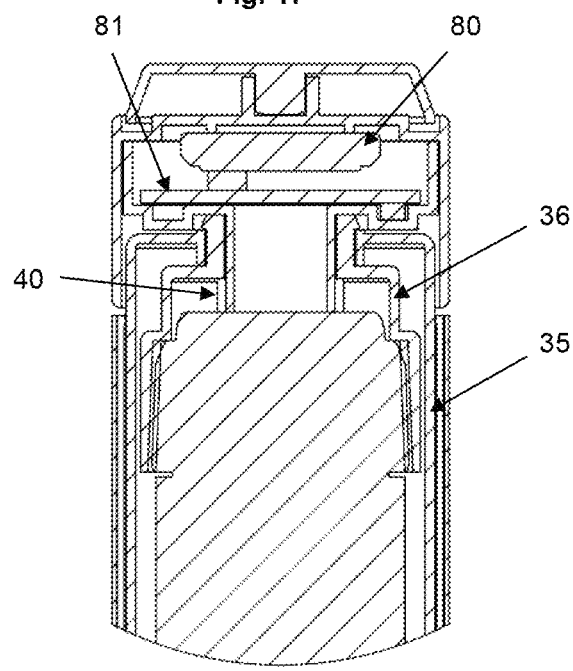
FIG. 17 a sectional view of the module of FIG. 14 in the dispensing mode.

As can be seen in FIGS. 16 and 17 the thrust bearing 46 between the coupler 36 and the tube 35 is optimized to reduce its diameter and therefore reduce the frictional torque loss at this interface during dispense (as compared to Embodiment 3).

Functionally this embodiment works in the same way as Embodiment 3. The sensor arrangement 45 and target arrangement is also functionally similar with the sensor arrangement 45 mounted on or in dial 37 and reading in a distal axial direction and being reflected by encoder features, namely regions of reflectivity 43, arranged on a proximal end face of the tube 35. The sensor of the sensor arrangement 45 can be active in either or both of dialing and dispensing. As previously described multiple different sensor technologies and arrangements could be applied, the illustrated optical system is an exemplary option.

It can be seen in FIGS. 16 and 17 that the tube 35 is retained by the coupler 36 in the region of the thrust bearing 46. This connection is axisymmetric such that relative rotation is possible whereas relative axial and radial movement is not possible.

Embodiment 5

Embodiment 5 is depicted in FIGS. 18 to 22. FIG. 18 shows an exploded view of the system, which is functionally similar to Embodiment 4. A body 47 affixes to the device housing 101 of the drug delivery device 100 and a tube 48 is non-rotational relative to the body 47 due to spline features 52 which engage with splines 53. A coupler 49 affixes to the device dial grip 103 and is enclosed within a dial 50 with an outer shell 50a and an insert 50b. A separate button 51 runs on a minimised thrust bearing 58 on the dial 50.

FIG. 19 further shows a different exploded view angle where the splines 53 are visible. Also in this view non-rotation features 55 are visible on the coupler 49 these engage with non-rotation features 56 of the insert 50b of dial 50 which are shown further in the view of just the dial 50, viewed from a distal direction, see FIG. 20.

Embodiment 5 is similar to Embodiment 4 except that the tube 48 is retained by the dial element 50 instead of the coupler. This leads to some packaging advantages, i.e. a smaller size, and it means that the sensor and target do not change distance to each other which makes the encoding more robust.

The embodiment is shown further in the two cross section views wherein FIG. 21 shows the dialing mode and FIG. 22 shows the dispensing mode. These figures show how the tube 48 is trapped and retained inside the dial 50 between the outer shell 50a and the insert 50b. A small diameter thrust bearing 58 is formed between the two elements to minimise the frictional drag induced in the system. It can also be seen that this is where the tube 48 is retained.

FIG. 22 shows the dispensing state where the button 104 of the drug delivery device 100 has been pressed, through movement of the module elements, it can be seen that all elements of the module, except the body 47 have travelled a distal distance equal to the button travel of the drug delivery device 100.

In FIGS. 21 and 22 a sensor arrangement 57 can be seen. This sensor arrangement 57 may be of any suitable technology that has previously been disclosed. In this example, the preferred arrangement is to have optical sensor(s) configured to face in a proximal direction, for the light to pass through a transparent region of the dial 50 and to be reflected from target surfaces 54 (regions of reflectivity) on a distal facing surface of the proximal end of the tube 48. The sensor(s) of sensor arrangement 57 can therefore detect relative rotation of the dial 50 and the tube 48 and can be active in either or both of dialing and dispensing.

Embodiment 6

Embodiment 6 is similar to the previous embodiments but has a clutch system introduced in order to be able to save the extra part of the button, this is achieved by a design such that the dial does not rotate during dispense. In addition, this embodiment is encoded to read rotation during dialing and infer the dose dispensed. With a small modification which will be explained below in more detail, it is also possible for the sensor to read rotation during dispensing.

Figure 23:
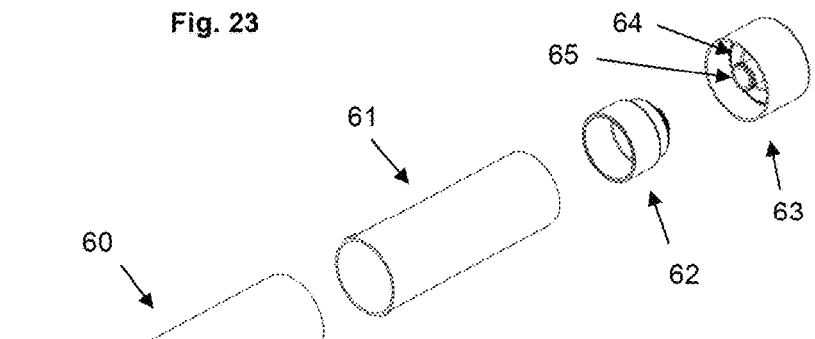
FIG. 23 shows an exploded view of an electronic add-on module according to a sixth embodiment.
Figure 24:
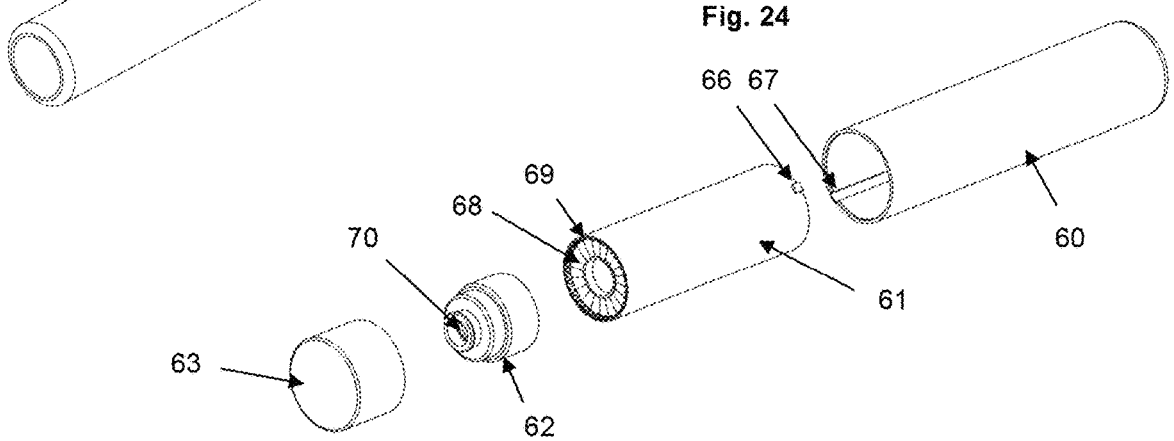
FIG. 24 shows an exploded view of components of the module of FIG. 23 from the opposite side.

FIGS. 23 and 24 show an exploded view of the module elements from opposite sides. A body 60 releasably affixes to the device housing 101 of the drug delivery device and a tube 61 is non rotatable relative to the body 60 due to the engagement of spline features 66 and splines 67. A coupler 62 is releasably attached to the device dial grip 103 of the drug delivery device and a dial 63 is arranged for the user to rotate to dial and push to dispense.

The dial 63 comprises an outer shell 63a and an insert 63b and has two sets of clutch teeth, inner clutch features 65 on the insert 63b that engage with the coupler 62 and outer clutch features 64 on the insert 63b that engage with the tube 61. FIG. 24 shows the clutch features 70 on the coupler 62 as well as the clutch features 69 on the tube 61 which both engage with the dial 63. Clutch features 65, 70 form a first clutch and clutch features 64, 69 for a second clutch. Reflective surfaces 68 are also shown in this figure which are described below.

Figure 25:
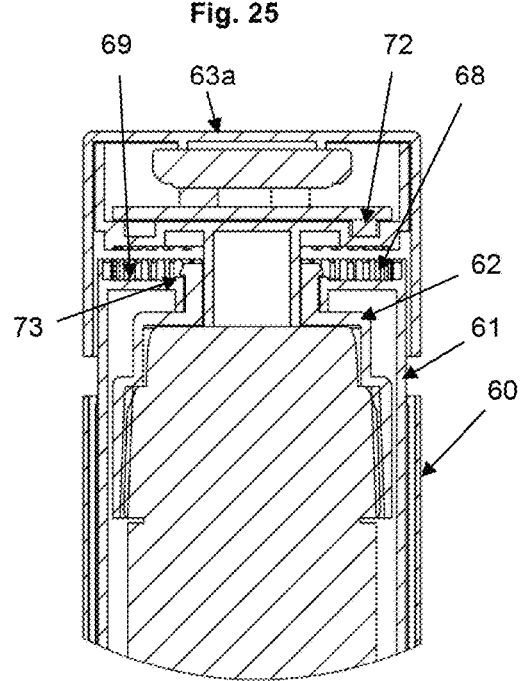
FIG. 25 a sectional view of the module of FIG. 23 in the dialing mode.

FIG. 25 below shows all elements of the module and the drug delivery device 100 when in the dialing state. In this view it can be seen that the first clutch 65, 70 between the coupler 62 and the dial 63 is engaged and the second clutch between the dial 63 and the tube 61 is disengaged, thus during dialing the coupler 62 and the dial 63 are rotationally locked together and rotate (and extend helically) with the device dial grip 103 of the drug delivery device. The tube 61 is permanently non-rotatable relative to the body 60, therefore there is relative rotation between the dial 63 and the tube 61 during dialing. A sensor arrangement 72 with sensor(s), can be seen mounted inside the dial 63 and is configured to read in a distal direction onto the proximal end surface of the tube 61 and read the reflective surfaces 68. It is to be noted that many different sensor technologies and arrangements could work with this embodiment. As an example, an optical reflective sensor technology may be used herein with two sensors reading a quadrature coded target. Alternating reflective and non-reflective surfaces could be achieved in a number of ways including black and white coloring and different axial distances to the sensor.

Similar to a number of the other embodiments the tube 61 can be seen to be restrained by clip features 73 to the coupler 62. This is an axial (and radial) constraint only and relative rotation is permitted at all times. This is designed to be a low friction interface, and optimized therefore to have a small diameter, such that losses during dispensing do not inter-fere with the drug delivery device dispensability.

Figure 26:
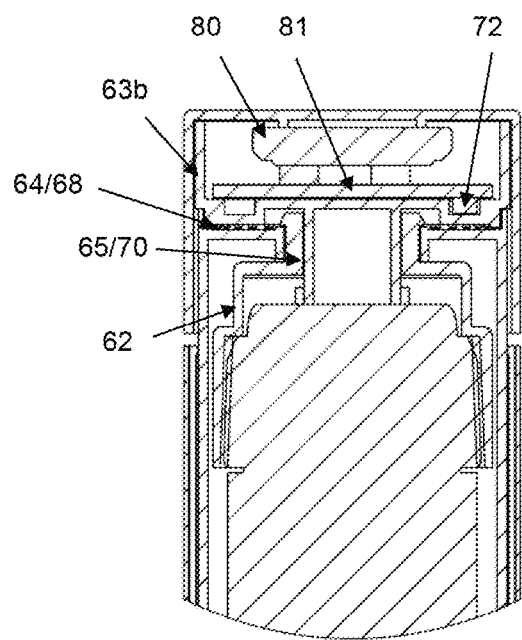
FIG. 26 a sectional view of the module of FIG. 23 in the dispensing mode.

FIG. 26 shows the configuration when the button 104 has been pressed and the system is in a dispensing state. In this mode it can be seen that both clutches have swapped state, the coupler 62 is now decoupled from the dial 63 and the dial 63 is now coupled to the tube 61. In this way during dispense the tube 61 and the dial 63 only travel back axially whereas the coupler 62 rotates (and travels helically) with the device dial grip 103 of the drug delivery device.

As mentioned this embodiment is encoded to read the dialing event and convert that into a dose event. As such it is desirable to provide suitable switches (not shown) in order that the electronics are awake and the sensors active during dialing and such that the axial travel of pressing the button is detected in order to convert the stored dialed value into a dispense event. However, it is also possible for the sensor to read through the tube 61 on to the coupler 62 to read rotation during dispensing. For this alternative, the reflective surfaces 68 depicted as being on the tube 61 have to be moved accordingly on to a proximally facing area of the coupler 62.

Examples for optical sensor arrangements and the respective working principles suitable for all embodiments of the electronic add-on module of the present disclosure are described e.g. in WO 2019/101962 A1, WO 2023/046787 A1 and WO 2023/099514 A1. Other sensor arrangements including an optical sensor, a magnetic sensor, a capacitive sensor and a mechanical sensor are also suitable for the electronic add-on module of the present disclosure.

In the Figures of all embodiments of the electronic add-on module of the present disclosure an electric power source 80, a circuit board assembly 81 electrically connected to the electric power source 80 and to the sensor arrangement(s) 9, 23, 33, 45, 57, 72 are depict-ed. While the power source 80 and the circuit board assembly 81 are depicted arranged on an insert of the dial and encased by an outer shell of the dial, other configurations or arrangements are possible.

In addition, at least one switch (not shown), e.g. a microswitch, may be provided for activating or waking up the electronic add-on module. The switch may be arranged on or within the dial such that the switch is actuated at the beginning of switching the electronic add-on module from its dialing mode into its dispensing mode. In addition or as an alternative, a switch may be provided which is actuated by relative rotational movement between the dial and a rotationally stationary component part, e.g. the tube, at the beginning of dose dialing.

REFERENCE NUMERALS 1, 12, 24, 34, 47, 60 body
2, 13, 25, 35, 48, 61 tube
3, 14, 26, 36, 49, 62 coupler
4, 15, 27, 37, 50, 63 dial
4a, 15a, 27a, 37a, 50a, 63a outer shell
4b, 15b, 27b, 37b, 50b, 63b insert
5, 8, 16, 17, 29, 39, 42, 52, 53, 66, 67 splines
6, 7, 19, 21, 65, 70 first clutch
9, 23, 33, 45, 57, 72 sensor
10, 11, 22, 43, 54, 68 regions of reflectivity
13a recess
14a flange
18, 20, 64, 69 second clutch
28, 38, 51 button
30 protrusion
31 recess
32, 41, 59 pin
46, 58 thrust bearing
73 clip feature
80 electric power source
81 circuit board assembly
100 drug delivery device
101 device housing
102 (dose) window
103 device (dose) dial grip
104 device (dose) button
I longitudinal axis (of the module)
II longitudinal axis (of the drug delivery)

The invention claimed is:

1. An electronic add-on module configured for releasable attachment to a drug delivery device which comprises a device housing and a device dial grip, the electronic add-on module comprising:
a body configured to be releasably attached to the device housing;
a coupler configured to be releasably attached to the device dial grip; and
a dial configured to be axially displaceable with respect to the coupler, wherein an electric power source, a circuit board assembly electrically connected to the electric power source, and a sensor arrangement electrically connected to the circuit board assembly are arranged in the dial,
wherein the electronic add-on module is configured to be switched between a dialing mode in which the dial is rotationally constrained to the coupler and a dispensing mode by an axial displacement of the dial relative to the body,
wherein the electronic add-on module further comprises a tube which is configured to be permanently rotationally constrained to the body and configured to be axially displaceable relative to the body and wherein the dial is configured to be rotatable relative to the tube at least in a dialing mode.

2. The electronic add-on module according to claim 1, wherein the body and the tube each comprise mating splines configured to permanently rotationally constrain the tube to the body and to permit axial displacement of the tube relative to the body.

3. The electronic add-on module according to claim 1, wherein the tube is axially constrained to the coupler or to the dial.

4. The electronic add-on module according to claim 1, wherein the coupler is rotatable relative to the tube.

5. The electronic add-on module according to claim 1, wherein the sensor arrangement comprises at least one non-contact sensor.

6. The electronic add-on module according to claim 5, wherein the at least one non-contact sensor is at least one optical sensor, wherein at least one of the coupler or the tube comprises regions of reflectivity and regions of absorption, and wherein the at least one optical sensor is configured and arranged to sense the regions of reflectivity.

7. The electronic add-on module according to claim 1, wherein at least a portion of the body, the tube and/or the dial is optically transparent.

8. The electronic add-on module according to claim 1, further comprising a first clutch for rotationally coupling and decoupling the coupler and the dial, wherein the electronic add-on module is configured to be switched between the dialing mode in which the dial is rotationally constrained to the coupler and the dispensing mode in which the dial is rotationally decoupled from the coupler.

9. The electronic add-on module according to claim 8, wherein the electronic add-on module is configured to be switched from the dialing mode into the dispensing mode by a distal axial displacement of the dial towards the body.

10. The electronic add-on module according to claim 1, further comprising a second clutch for rotationally coupling and decoupling the tube and the dial, wherein, in the dispensing mode of the electronic add-on module, the tube and the dial are rotationally constrained.

11. The electronic add-on module according to claim 1, further comprising a button arranged at a proximal end of the dial and guided therein such that the button is rotatable with respect to the dial.

12. The electronic add-on module according to claim 1, wherein the dial is a dial button with a proximal actuation end face.

13. The electronic add-on module according to claim 1, wherein the body comprises on an inner side of the body at least one elastomeric grip and/or at least one mechanical clip configured to be releasably attached to the device housing.

14. The electronic add-on module according to claim 1, wherein the coupler comprises on an inner side of the coupler at least one elastomeric grip and/or at least one mechanical clip configured to be releasably attached to the device dial grip.

15. The electronic add-on module according to claim 1, wherein the circuit board assembly and the sensor arrangement are adapted and configured to detect or calculate a dose set by a user in the dialing mode, a dialing start point, a dialing end point, a dispensing start point, a dispensing end point and/or a dose amount ejected from the drug delivery device in the dispensing mode.

16. The electronic add-on module according to claim 1, further comprising a switch electrically connected to the electric power source and/or the circuit board assembly, wherein the switch is configured to be operated when the electronic add-on module is switched from the dialing mode into the dispensing mode and/or when the drug delivery device is dialed.

17. An assembly comprising: a drug delivery device comprising a device housing and a device dial grip which is rotatable relative to the device housing for setting a dose; and an electronic add-on module configured for releasable attachment to the drug delivery device, the electronic add-on module comprises at least: a body configured to be releasably attached to the device housing; a coupler configured to be releasably attached to the device dial grip; and a dial configured to be axially displaceable with respect to the coupler, wherein an electric power source, a circuit board assembly electrically connected to the electric power source, and a sensor arrangement electrically connected to the circuit board assembly are arranged in the dial, wherein the electronic add-on module is configured to be switched between a dialing mode in which the dial is rotationally constrained to the coupler and a dispensing mode by an axial displacement of the dial relative to the body, wherein the electronic add-on module further comprises a tube which is configured to be permanently rotationally constrained to the body and configured to be axially displaceable relative to the body and in that the dial is configured to be rotatable relative to the tube at least in the dialing mode.

18. The assembly of claim 17, wherein the body comprises on an inner side of the housing at least one elastomeric grip and/or at least one mechanical clip configured to be releasably attached to the device housing.

19. The assembly of claim 17, wherein the coupler comprises on an inner side of the coupler at least one elastomeric grip and/or at least one mechanical clip configured to be releasably attached to the device dial grip.

20. The assembly of claim 17, wherein the drug delivery device comprises a drug container that contains a drug.

* * * * *